(12) United States Patent
Solioz et al.

(10) Patent No.: US 10,786,571 B2
(45) Date of Patent: Sep. 29, 2020

(54) HYDROPHILIC GEL FOR TOPICAL DELIVERY OF 5-AMINOLEVULINIC ACID

(71) Applicant: Zimmer Biotech GmbH, Neu-Ulm (DE)

(72) Inventors: Andre Solioz, Basel (CH); Frank Stowasser, Basel (CH); Armin Zimmer, Neu-Ulm (DE)

(73) Assignee: Zimmer Biotech GmbH, Neu-Ulm (DE)

( * ) Notice: Subject to any disclaimer, the term of this patent is extended or adjusted under 35 U.S.C. 154(b) by 0 days.

(21) Appl. No.: 15/761,623

(22) PCT Filed: Sep. 20, 2016

(86) PCT No.: PCT/EP2016/072296
§ 371 (c)(1),
(2) Date: Mar. 20, 2018

(87) PCT Pub. No.: WO2017/050759
PCT Pub. Date: Mar. 30, 2017

(65) Prior Publication Data
US 2018/0344852 A1    Dec. 6, 2018

(30) Foreign Application Priority Data

Sep. 21, 2015 (EP) .................................... 15186006

(51) Int. Cl.
| | | |
|---|---|---|
| *A01N 43/00* | (2006.01) | |
| *A01N 43/46* | (2006.01) | |
| *A61K 31/55* | (2006.01) | |
| *A61K 41/00* | (2020.01) | |
| *A61K 9/00* | (2006.01) | |
| *A61K 9/06* | (2006.01) | |
| *A61K 47/36* | (2006.01) | |
| *A61P 17/00* | (2006.01) | |
| *A61K 31/198* | (2006.01) | |
| *A61K 47/22* | (2006.01) | |

(52) U.S. Cl.
CPC ........ *A61K 41/0061* (2013.01); *A61K 9/0009* (2013.01); *A61K 9/0014* (2013.01); *A61K 9/06* (2013.01); *A61K 31/198* (2013.01); *A61K 47/22* (2013.01); *A61K 47/36* (2013.01); *A61P 17/00* (2018.01)

(58) Field of Classification Search
None
See application file for complete search history.

(56) References Cited

U.S. PATENT DOCUMENTS

| | | |
|---|---|---|
| 5,910,489 A | 6/1999 | Falk et al. |
| 6,723,750 B2 * | 4/2004 | Voet ..................... A61K 31/195 514/185 |
| 2007/0128287 A1 | 6/2007 | Inagaki et al. |
| 2007/0142343 A1 | 6/2007 | Gans et al. |
| 2008/0227757 A1 | 9/2008 | Muller-Goymann et al. |
| 2012/0283328 A1 | 11/2012 | Modi |
| 2013/0330373 A1 | 12/2013 | Lee |

FOREIGN PATENT DOCUMENTS

| | | |
|---|---|---|
| DE | 102009041048 A1 | 3/2011 |
| EP | 1716845 A1 | 11/2006 |

OTHER PUBLICATIONS

Office Action (6 pages) and Search report (2 pages) in corresponding RU application 2018109412 dated Mar. 27, 2019.
International Search Report dated Nov. 29, 2016 issued in corresponding PCT/EP2016/072296 application (4 pages).
English Abstract of DE 102009041048 A1 published Mar. 24, 2011.

* cited by examiner

*Primary Examiner* — Layla Soroush
(74) *Attorney, Agent, or Firm* — Millen White Zelano and Branigan, PC; John Sopp (57) ABSTRACT

The present invention relates to a pharmaceutical topical gel solution that contains 5-aminolevulinic acid (5-ALA) and an aqueous low viscous gel matrix. This invention also relates to a pharmaceutical preparation containing this composition. The formulation of this type can be used in photodynamic therapy as well as in the photodynamic detection of abnormally proliferating cells.

15 Claims, 6 Drawing Sheets

HYDROPHILIC GEL FOR TOPICAL DELIVERY OF 5-AMINOLEVULINIC ACID

FIELD OF THE INVENTION

The present invention relates to a pharmaceutical topical gel solution that contains 5-aminolevulinic acid (5-ALA). This invention also relates to a pharmaceutical preparation containing this composition. The formulation of this type can be used in photodynamic therapy as well as in the photodynamic detection of abnormally proliferating cells.

BACKGROUND OF THE INVENTION

The world is currently experiencing steadily increasing cancer rates that are largely due to the steadily advancing age of populations in large, industrialized nations and changing lifestyles. Because the rates of many cancers are steadily increasing, this brings a high demand for more and higher quality treatments. Of the various types of pre-cancer and cancers, pre-cancerous lesions such as Actinic Keratosis and other types of non-melanoma skin cancer continue to be a serious and increasing issue in countries with large populations of white people with fair complexions (blond hair, blue eyes) and/or a high exposure to UV radiation.

Photodynamic therapy is a fast growing and promising therapeutic method for treating those premalignant and malignant diseases which are connected to cell proliferation. 5-ALA has been used for more than two decades in commercial products due to its high safety factor based on its endogenous nature, non-toxicity and selectivity for cancerous cells. It is known as a second generation photosensitizer, since the sensitivity to daylight after treatment is dramatically reduced to only 1-2 days in comparison to the 30-60 days of the still marketed Photofrin® (Porfimer Sodium).

For therapeutic purposes 5-ALA is administered topically or systemically and penetrates non-selectively into all cells, where it is metabolized to an active sensitizer PPIX (Protoporphyrin IX) utilizing the heme biosynthesis pathway. As cancerous or neoplastic (fast-growing) cells commonly have lower intracellular iron ($Fe^{2+}$) levels than normal, healthy cells, PPIX cannot be quickly converted to its final product heme and therefore accumulates only within cancer cells.

Since PPIX is a potent photosensitizer this metabolic pathway can be exploited in Photodynamic Therapy (PDT). This is an already approved therapeutic strategy making 5-ALA one of the most successful prodrugs used in treatment of a wide range of pre-cancerous and cancerous lesions. (M. Wachowska et al, Aminolevulinic Acid as a Prodrug in Photodynamic Therapy of Cancer, Molecules 2011, 16, 4140-4164).

After selective accumulation of the photosensitizer in the tumor it can be activated by illumination using light of the appropriate wavelength and dose.

The PPIX molecule absorbs the light and the absorbed energy is subsequently transferred to molecular oxygen, creating the singlet state oxygen $^1O_2$. The singlet oxygen that is generated from the PDT process on PPIX is then resulting in oxidative damage to intracellular macromolecules and consequently leads to cell death. This cytotoxic effect, in particular on proliferating cells, stems from reactions of the singlet oxygen with for example the cell membrane and the mitochondria or triggers the formation of cell-damaging free radicals. The mode of PDT-induced cell death is usually a mixture of apoptosis, necrosis and autophagy. It is generally agreed that apart from the direct cellular cytotoxicity, two other important factors contribute to the overall PDT effect: the vascular shutdown (which stops angiogenesis and thus prevents metastasis) and the local inflammatory reaction.

In addition to 5-ALA, the wavelength of light chosen to perform the PPIX excitation is quite important as is the penetration depth of the 5-ALA itself into the affected tissue. For purely superficial treatment, the wavelength of maximum absorption is generally considered to be the best for treatment. However, for deeper lesions, a compromise between excitation and penetration depth of the light must be reached, which usually means a shift to longer (i.e. more red) wavelengths. 5-ALA is a polar molecule and occurs in physiological conditions as a charged Zwitterion. This accounts for its low lipid solubility and this ultimately limits the penetration through the outermost skin layer, the stratum corneum, which is of lipidic nature.

Furthermore, irradiation of the photosensitizer gives rise to a characteristic fluorescence radiation which can be used for detection proliferating cells.

A number of investigations using topically applicable 5-aminolevulinic acid compositions are known from the prior art. While these investigations have the feature in common that the 5-aminolevulinic acid or derivatives thereof employed, differences exist with regard to other parameters, such as period of penetration, period of treatment, type of light employed and the dose of light applied.

Although the investigations disclosed in the prior art clearly demonstrate the potential of photodynamic therapy using 5-aminolevulinic acid, the different formulations already marketed suffer from a number of disadvantages.

General importance for the development of a PDT therapy is the guideline for Photosensitizers in clinical PDT (RR Allison et al, Photodiagnosis and Photodynamic Therapy (2004) 1, 27-42) which has defined relevant points that need to be considered. Among them the most important requirements the product needs to fulfill are listed:

- Non-toxic and no toxic or cancerogenous by-products should be formed; otherwise chemotherapeutic agents can be used
- Easy removal is mandatory (short half-life of the photosensitizer)
- Needs to easily penetrate into the skin, deep enough to reach the entire cancerous tissue and reliably and selectively accumulate within the mitochondria of the cancer cells for effective induction of apoptosis when illuminated
- Reliable activation by an appropriate wavelength of light is needed to prevent accidental treatment
- Hours or only few days of photosensitivity of the entire skin after treatment are preferred over several weeks or months
- Versatile by topical, swallowing, inhalation or IV, without causing of side effects like e.g. allergic reactions or hypertension
- Must get where you need it and activate when you need it, each and every time
- Longer wavelengths of activation allow for deeper tissue penetration
- The ability to be used in conjunction with other forms of treatment such as surgery, radiation, and chemotherapy
- Should easily permit treatment overdosage of illumination without causing side effects
- Easily and safely administered, targets the appropriate structure, avoids normal tissues, activates when needed until the structure in question is destroyed and then eliminates itself without causing permanent damage to the rest of the body.

In particular valid for 5-ALA is that it is known to degrade in aqueous solution however it has to be stable for the period of usage in order to be therapeutically useful. Aqueous solutions show best stability below pH<6 (V. von Arx et al. (J. Pharm. Pharmacol. 49: 652-656, 1997)).

Another disadvantage is that the depth to which the photosensitizer penetrates into the damaged tissue is compromised by its low lipid solubility. As a result, the diseased tissue is in many cases only accessible to the photodynamic therapy in its superficial layers even though the depth to which the light employed for activating the photosensitizer penetrates would also enable more deeply lying layers to be treated.

Beside the depth of penetration the kinetic of the distribution within the skin and further on the metabolization to PPIX within the cells is relevant for patients and physicians. Current treatments achieve only after several hours incubation time clinical relevant PPIX accumulation for PDT treatment whereas faster treatment times would be highly desirable (T. Maisch et al. (Experimental Dermatology, 17, 813-820).

OBJECT OF THE INVENTION

The object of the present invention therefore is to provide a composition comprising 5-ALA which overcomes the disadvantages known from prior art products and which provides an improved penetration of 5-ALA into a patient's tissue and, at the same time, provides an adequate stability of 5-ALA. It is a still further object of the present invention to provide a composition comprising 5-ALA, which efficiently achieves rapid accumulation of PPIX after administration to a patient.

SUMMARY OF THE INVENTION

These objects are achieved by a composition according to the present invention comprising
a) 5-ALA or its HCl salt as an active ingredient;
b) a first penetration enhancer selected from one or more water-miscible ether compounds, preferably non-ethoxylated water-miscible ether compounds; and
c) a second penetration enhancer selected from one or more glycosaminoglycan compounds.

The inventors surprisingly found that a two-step approach may result in an unexpectedly increased penetration of 5-ALA into deep tissue layers. In the first step, a chemical penetration enhancer selected from one or more water-miscible ether compounds, preferably non-ethoxylated water-miscible ether compounds which changes the partition coefficient of the stratum corneum to enable hydrophilic molecules to penetrate into the skin, is used. By this approach, components a) and c) are allowed to penetrate the stratum corneum much better than as it has been disclosed in prior art compositions.

The term "non-ethoxylated" means ether compounds that were not ethoxylated by using ethylene oxide.

Once these components have passed the stratum corneum into the epidermis, the second penetration enhancer, i.e. one selected from one or more glycosaminoglycan compounds, allows the 5-ALA or its HCl salt to penetrate into the dermis by hydration of the basal layer cells. Hydration of the basal layer is necessary to promote opening of tight junctions to allow paracellular transport of 5-ALA.

This two-step, synergistic approach has been closely adapted to the characteristics of the diseased skin (for example affected by actinic keratosis) which is known to be dry, scaly and rough. The present composition therefore makes it possible for 5-ALA or its HCl salt to maximally penetrate into the skin even without any occlusion of the treated area being needed.

Occlusion is usually performed in topical PDT using currently marketed products like Metvix® or Ameluz®, representing galenical forms that contain a high level of oils and fats.

At increased ambient temperatures (like e.g. during summertime) these oily/fatty products show a tendency to liquify under occlusion leading to smearing out of the desired treatment area and hence decrease their effectivity. Even more severe they can drip down a patient's face, when areas on the forehead are treated, leading to contamination of other areas of the face like the eyes, where it causes strong discomfort of the patient leading to reduced patient compliance. Another product, Alacare®, is even an occlusive patch formulation itself.

DESCRIPTION OF THE FIGURES

In the Figures, the following is shown.

DETAILED DESCRIPTION OF THE INVENTION

In a preferred embodiment, the composition according to the present invention comprises 5 ALA in the form of its hydrochloride salt (5-ALA HCl) and is contained in the composition in a concentration range of 5-30 wt. %. An even more preferred concentration range of 5-ALA HCl is about 10-25 wt. % each based on the overall weight of the composition.

The composition of the present invention preferably is a composition for pharmaceutical use and thus, will contain one or more pharmaceutically acceptable auxiliaries. Those auxiliaries are, for example, selected from gel-forming polymers, in particular polymers for forming a hydrogel.

These types of polymers may be selected (but are not restricted to) hydrogels forming highly absorbent natural or synthetic polymeric networks which might include polyvinyl alcohol, sodium polyacrylate, acrylate (co)polymers or natural hydrogel materials such as agarose, methylcellulose, hyaluronic acid/hyaluronate. Other gel-forming polymers are hydroxypropylcellulose, methylhydroxyethylcellulose or sodium carboxymethylcellulose. A further polymer is xanthan gum.

For further information, it is referred to Rudolf Voigt, Pharmazeutische Technologie, 11$^{th}$ Edition, 2010, in particular page 396 and subsequent pages.

Other auxiliaries which might be used in a pharmaceutical composition according to the present invention are substances for preserving the composition, chelating agents, buffering agents and/or acidity regulators.

As usual preservatives, para-hydroxybenzoic acid esters such as methylparaben, ethylparaben or propylparaben (or sodium salts thereof and also in combination) can be used or, alternatively, potassium sorbate or sorbic acid. A preserving activity can also be achieved by using alcoholic additives such as, for example, those containing more than 15% of propylene glycol or glycerol.

Further auxiliaries might be selected from humidifying agents such as glycerol, propylene glycol or sorbitol, preferably in concentrations of 10-20 wt % based on the overall weight of the composition. These ingredients will prevent the hydrogel from drying out and enhance the applicability of the final pharmaceutical product.

Furthermore, the pharmaceutical composition of the present invention, in case of a hydrogel, might contain acidity regulators which ensure a suitable pH value. As mentioned above, 5-ALA degrades in aqueous solution and show best stability below pH values of 6. Therefore, it is a suitable approach to adapt the pH value of the overall composition to this pH range, for example by setting the pH value to a well-tolerated range of 3.5-4.5 by suitable ingredients. Those ingredients might be selected from different kinds of acids or acidic salts such as trisodium citrate dihydrate.

Further auxiliaries for use in a hydrogel of the present invention are chelating agents such as EDTA and buffering agents should that be required.

Further auxiliaries in addition to the ones listed above might be included in the composition as well. Regarding compositions different from topical compositions in form of hydrogels it is generally referred to pharmaceutical standard literature such as Remington, the Science and Practice of Pharmacy, $22^{nd}$ Edition, 2013.

Preferably, the hydrogel takes the form of a low viscous hydrogel. The term "low viscous" is generally defined herein as describing a viscosity of between (and including) 1,000 and 13,000 mPas measured at 32° C. The viscosity can be measured using a cone/plate Rheometer (Rheostress RS-1, Thermo Haake, Karlsruhe, Germany), with the geometry 35 mm, cone angle 2°, in oscillatory mode using constant deformation at 1 Hz and Auto-Strain. The measurement is performed by applying a linear temperature-ramp from 20° C. to 40° C. at a rate of 1° C./min, using the built in peltier element of the Rheometer. Viscosity readings [mPas] were taken from the resulting curve at 25 and 32° C., the latter representing the average skin surface temperature.

A preferred range of viscosity for the low viscous hydrogel is about 3,000-7,000 mPas.

According to a more preferred embodiment, the pharmaceutical composition of the present invention contains one or more water miscible ether compounds, preferably non-ethoxylated water miscible ether compounds selected from isosorbide based compounds, preferably from 1,4:3,6-dianhydrosorbitol 2,5-pentylethylether (pentylethyl isosorbide), 1,4:3,6-dianhydrosorbitol 2,5-laurylglycerylether (laurylglyceryl isosorbide) and 1,4:3,6-dianhydrosorbitol 2,5-dimethylether (dimethyl isosorbide). This group of ether compounds serves as a chemical penetration enhancer which changes the partition coefficient of the stratum corneum and by this enables hydrophilic molecules to penetrate the skin. The suitable concentration ranges of these ether compounds are usually in a range of about 4-15 wt. %, more preferably in the range of 8-12 wt. % based on the overall weight of the composition.

The one or more glycosaminoglycan compounds forming the hydrophilic intradermal penetration enhancer are preferably selected from chondroitin sulfate, keratan sulfate, dermatan sulfide, heparin sulfate, heparan sulfate and/or hyaluronic acid/sodium hyaluronate. The group of hyaluronic acid and its sodium salt is also termed "non-sulfated glycosaminoglycan".

In a preferred embodiment, the composition of the present invention comprises a first penetration enhancer selected from one or more non-ethoxylated water miscible ether compounds and a second penetration enhancer selected from one or more isosorbide based compounds.

These compounds usually are added to the composition of the present invention (based on the overall weight of the composition) in a concentration range of 0.5-1.5 wt. %, more preferably in the range of 0.8-1.2% wt.

In one preferred embodiment, the pharmaceutical composition of the present invention is a low viscous hydrogel and contains 5-ALA HCl, dimethyl isosorbide and sodium hyaluronate. Optional auxiliaries are trisodium citrate as a pH regulating agent, disodium edetate as a chelating agent, methyl and propylparaben as preservatives and Xanthan gum as viscosity enhancer. Further, the hydrogel contains purified water of pharmaceutical grade.

In this preferred composition, 5-ALA HCl is present in an amount of about 20% by weight, dimethylisosorbide is contained in an amount of about 10 wt. % and sodium hyaluronate in an amount of about 1% by weight based on the overall weight of the composition (including water).

The topical pharmaceutical composition according to the present invention might be formulated in an apparatus for applying 5-ALA containing hydrogels such as a two chamber system that separates the active ingredient 5-ALA from the gel matrix (which is contained in a separate chamber) wherein both chambers are mixed prior to treatment by breaking a seal that separates both chambers to give a ready-to-use topical gel solution that can be focused on the area of application on the skin.

The hydrogel thus may be stored in a double chamber system which might be made of a transparent, laminated polymer consisting of two chambers separated by a breakable wall. The material chosen protects the sensitive active ingredient in one chamber from oxygen and water, thus providing long-term stability to 5-ALA, while in the other chamber the matrix of the hydrogel is stored. It was observed that the 5-ALA ingredient was long-term stable at different storage conditions without degradation in such a double chamber tube.

For example, the seal which separates the two chambers can be broken by applying pressure to the liquid containing chamber which leads to breakage of the seal. Once the seal is open, the resulting slurry needs to be vigorously kneaded until a clear gel results. After this procedure, the product is ready for final application to the patient's skin.

The composition of the present invention is used in the photochemotherapeutic treatment or diagnosis of disorders or abnormalities of internal or external surfaces of the body. These disorders or abnormalities are selected from pre-cancer and cancers, pre-cancerous lesions of the skin such as actinic keratosis and other types of non-melanoma skin cancer, SCC (squamous cell carcinoma), or BCC (basal cell carcinoma).

The present invention now is described by the following examples which illustrate the present invention:

EXAMPLES

Formulation trials were carried out to further meet above stated requirements for topically applied photosensitizers. The examples according to the invention were prepared in a Two-Step process as follows:

Step I: Disodium edetate (Komplexon III, Merck, Darmstadt) was dissolved in purified water at room temperature, about 22° C., under stirring using a magnetic stirring motor (IKAMAG RT 15, IKA Werke, Germany) at a stirring rate of 300 rpm for 5 min. To the resulting solution, sodium hyaluronate (HA-EP$_1$, 760 KDa, Shandong Freda Biopharm Co., Ltd, Jinan, China) was added and dispersed using a glass stick in slow circular movements for 1 min. The resulting dispersion was kept in the fridge at 2-8° C. for 12-18 hrs. After this period the sodium hyaluronate was fully swollen and the resulting preparation had a clear and viscous aspect.

Step II: Methylparaben and propylparaben (Sigma-Aldrich Chemie GmbH, Buchs, Switzerland), if present, were dissolved in dimethyl isosorbide (Dottisol®, Dottikon Exclusive Synthesis, Dottikon, Switzerland) under stirring using the magnetic stirring motor as previously used at a stirring rate of 300 rpm for 10 min at room temperature, about 22° C. The resulting clear solution was added to Step I under stirring, using the magnetic stirring motor as previously used, at a stirring rate of initially 300 rpm. The stirring rate was gradually increased to 700 rpm within 20 min at room temperature, about 22° C., to result in a clear gel.

To this clear gel, trisodium citrate dihydrate (Sigma-Aldrich Chemie GmbH, Buchs, Switzerland) was slowly (within 1 min) added under stirring using the magnetic stirring motor as previously used, at a stirring rate of 700 rpm and stirring at the same rate was continued for 30 minutes at room temperature, about 22° C. If present, Xanthan gum (Type: FNCS, Jungbunzlauer, Basel, Switzerland), was then added during mixing using a rotor/stator homogenizer (Polytron PT 10-35 GT, Kinematica, Switzerland) at 5000 rpm for 20 min at room temperature, about 22° C., until a homogeneous gel results.

For the final product the matrix gel is mixed with an appropriate amount of 5-ALA (ingredient a).

The viscosity was measured using a cone/plate Rheometer (Rheostress RS-1, Thermo Haake, Karlsruhe, Germany), with the geometry 35 mm, cone angle 2°, in oscillatory mode using constant deformation at 1 Hz and Auto-Strain. The measurement was performed by applying a linear temperature-ramp from 20° C. to 40° C. at a rate of 1° C./min, using the built in peltier element of the Rheometer. Viscosity readings [m Pas] were taken from the resulting curve at 25 and 32° C., the latter representing the average skin surface temperature.

The numbers in table 1 and 2 below represent % by weight of total product. The following compounds were used in the compositions:
a) 5-ALA HCl: active ingredient
b) Dimethyl Isosorbide: surface penetration enhancer
c) HA-Na LMW: (Sodium hyaluronate, Low Molecular Weight) intradermal penetration enhancer
d) Trisodium citrate: pH regulating agent
e) Disodium edetate: metal chelating agent
f) Methylparaben: preservative
g) Propylparaben: preservative
h) Xanthan gum: viscosity enhancer
i) Purified water: filler

TABLE 1

| | Ex. 1 | Ex. 2 | Ex. 3 | Ex. 4 | Ex. 5 | Ex. 6 |
|---|---|---|---|---|---|---|
| 5-ALA HCl | 20 | 20 | 20 | 20 | 20 | 20 |
| Dimethyl Isosorbide | — | 15 | — | 4 | 11 | — |
| HA-Na LMW | — | — | 1 | 1 | 1 | 2 |
| Trisodium citrate | 12 | 12 | 12 | 12 | 12 | 12 |
| Disodium edetate | — | — | — | — | — | — |
| Methylparaben | — | — | — | — | — | — |
| Propylparaben | — | — | — | — | — | — |
| Xanthan gum | 0.5 | 0.5 | 0.5 | 0.5 | 0.5 | 0.5 |
| Purified water | 67.5 | 52.5 | 66.5 | 62.5 | 57.5 | 65.5 |
| Viscosity at 25° C. [mPas] | 2300 | 3450 | 5300 | 7750 | 3000 | 12850 |
| Viscosity at 32° C. [mPas] | 2180 | 3350 | 4600 | 6650 | 2400 | 11300 |

| | Ex. 7 | Ex. 8 | Ex. 9 | Ex. 10 | Ex. 11 |
|---|---|---|---|---|---|
| 5-ALA HCl | 20 | 20 | 20 | 20 | 20 |
| Dimethyl Isosorbide | — | — | 15 | 15 | 10 |
| HA-Na LMW | — | 0.5 | 0.5 | 1.5 | 1 |
| Trisodium citrate | 12 | 12 | 12 | 12 | 12 |
| Disodium edetate | 0.02 | 0.02 | 0.02 | 0.02 | 0.02 |
| Methylparaben | 0.1 | 0.1 | 0.1 | 0.1 | 0.1 |
| Propylparaben | 0.03 | 0.03 | 0.03 | 0.03 | 0.03 |
| Xanthan gum | 0.8 | 0.3 | 1.0 | — | — |
| Purified water | 67.05 | 67.05 | 51.35 | 51.35 | 56.85 |
| Viscosity at 25° C. [mPas] | 6600 | 2000 | 6200 | 6800 | 4100 |
| Viscosity at 32° C. [mPas] | 6600 | 1750 | 6100 | 5700 | 3900 |

To estimate the ideal ratios of the two penetration enhancers, a design of experiments, according to regulatory (ICH) requirements for a Quality by Design (QbD) approach, was performed.

Figure 1:
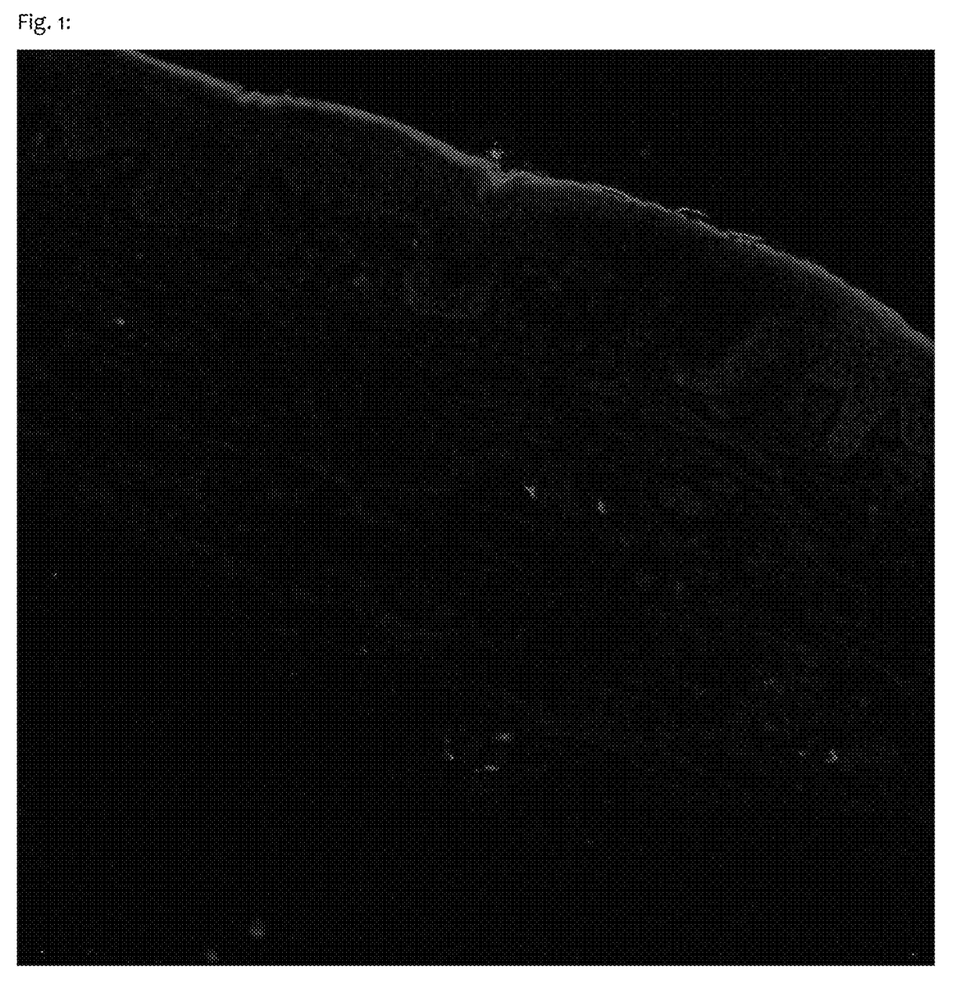
FIG. 1—depicts an untreated pig ear image reflecting natural porphyrin fluorescence.
Figure 2:
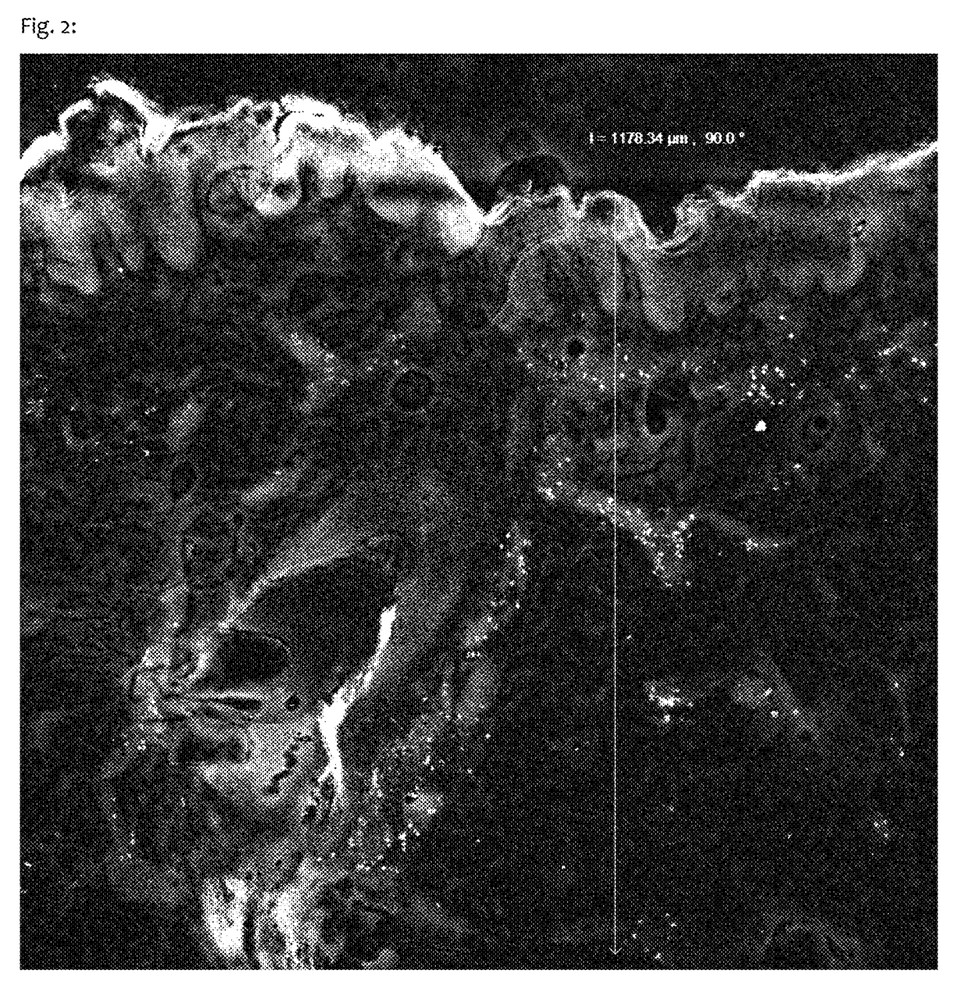
FIG. 2—depicts porphyrin fluorescence images (Example 11 Table 1) reflecting the penetration depth of the formulation of the present invention into the pig ear after an incubation period of 4 hrs.

As part of the development, ex vivo testing on pig ear skin has been performed to assess the penetration depth and surprisingly it was found that very significant penetration depths could be achieved by using the composition of the present invention (>1 mm, FIG. 2). The greater penetration depths were particularly surprising because it had previously been assumed that, due to its hydrophilicity, 5-aminolevulinic acid would in any case be not readily able to penetrate through the epidermis.

Another surprising advantage is that, by using the second penetration enhancer, in accordance with the invention, 5-aminolevulinic acid is evidently taken up through basal membrane into the dermis.

Also as part of the development, time resolved ex vivo testing on pig ear skin has been performed to study the distribution and metabolization kinetics.

In these trials, much shorter incubation times were applied and the resulting fluorescence signal (average pixel intensity) was energy-dispersive recorded, each energy channel comprising a 5 nm bandwidth within the entire detection range of 584-716 nm. According to the unique fluorescence emission spectrum of Porphyrins (Uro/Coproporphyrin and PPIX), only the values from 614 nm to 643 nm were selected and are displayed in FIGS. 3 and 4 (graphics by using the Microscope software (ZEN Black, Release Version 8.1, ZEISS AG, Oberkochen, Germany)).

The integrated intensity values (as average pixel intensity) of the epidermal layer for the respective wavelength range are shown in Table 2. Beside Example 12, the commercially available product Levulan® Kerastick was incubated and measured. One ampule of Levulan® Kerastick contains 1.5 mL of solution vehicle comprising alcohol USP (ethanol content=48% v/v), water, laureth-4, isopropyl alcohol, and polyethylene glycol. The other ampule contains 354 mg of ALA HCl as a dry solid.

TABLE 2

| | EX. 12 | Levulan ® Kerastick |
|---|---|---|
| 5-ALA HCl | 20 | Commercially available |
| Dimethyl Isosorbide | 10 | product, |
| HA-Na LMW | 1 | contains |
| Trisodium citrate | 12 | 20 wt. % 5-ALA HCl |
| Disodium edentate | 0.02 | |
| Methylparaben-Na | 0.075 | |
| Propylparaben-Na | 0.025 | |
| Purified water | 56.88 | |
| Incubation period | Epidermal area of the sample Average pixel intensity for Uro/Coproporphyrin and PPIX (614-643 nm) | |
| 15 Min. Incubation | 3.01 | 1.97 |
| 60 Min. Incubation | 7.16 | 5.38 |

The surprising advantage is that after 15 min incubation time already significant amounts of Porphyrins could be detected in the epidermal layer and in comparison to the commercially available product a much higher concentration of Porphyrins could be reached. After 60 min incubation time the result for the example as described in this invention is larger than the respective values of the commercially available product.

According to the invention, the formulation comprises an active substance which is 5-aminolevulinic acid in its hydrochloride salt form which is converted in a cell into Protoporphyrin IX. The matrix is an essentially aqueous phase which is optimal for dermal applications and the pH adjusted for treatment is in an acceptable and well tolerated range between pH 3.5 to pH 4.5. This pH range guarantees stability of the product for 24 hours in order to be used therapeutically. The adjusted viscosity led to a rather low viscous gel for final mixture at 32° C. (skin temperature) of a range of 3000-5000 mPas. This viscosity allows easy spreading of the gel over the application area and exploring also hard to reach skin surfaces while it has enough adhesion to the skin that it stays on the skin without spreading uncontrolled.

Results

Ex vivo trials were performed on pig-ear skin considering the following standard literature:

W. Meyer, Dermatologist 47. 178-182, 1996; Meyer et al, Münch Tierarztl Wschr. 114: 92-99, 2001; Meyer et al., Münch Tierarztl Wschr 114: 100-111, 2001)

Patent WO 2004092726 A1

Biana Godin, Elka Touitou Transdermal skin delivery: Predictions for humans from in vivo, ex vivo and animal models Histochemical Techniques, JD Bancroft Pig ear skin is described to be the closest approach in comparison to human skin with regard to physiological and dimensional aspects. The human epidermis thickness is described to be 0.08 to 0.12 mm. There is no subcutaneous fatty tissue in pig ear skin in comparison to human skin, the pictures depicted are only consisting of a dermal layer below the epidermal layer.

Pig ears were taken from freshly slaughtered pigs (Süddeutsches Schweinefleischzentrum Ulm Donautal GmbH, Germany). The pig ears were cut, before washing of the entire pig using hot water, in order to leave the skin as intact as possible.

A defined amount of drug product was applied on a marked, square-shaped area of the pig-ear skin and the entire pig ear was then incubated in a Heracell 150i Incubator (Thermo Scientific, Waltham, USA) at 37° C. After 4 h, the pig ears were taken out from the Incubator and the previously marked areas, containing the drug product, were cut out, using a scalpel.

The resulting patch of pig-ear skin was then embedded in embedding media for cryotoms (Nr. 020108926; Leica Instruments, Nussloch). After freezing of the embedded patches at −20° C., vertical slices of a defined thickness were prepared using a Cryo Microtome (CM-30505, Leica Instruments, Nussloch). These slices were then fixated on glass slides using glycerol jelly (Glycerol Gelatin aqueous slide mounting medium, Sigma-Aldrich, St. Louis, USA). These samples were then stored at −40° C.

By a confocal laserscanning microscope (CLSM 510 Meta ZEISS AG, Oberkochen, Germany), using a lox objective (10×0.3NA EC Plan-Neofluar Phi M27, ZEISS AG, Oberkochen, Germany) the pictures as shown in the Figures were taken. The picture size illustrates top layer pig ear skin as resulting by the chosen magnification objective of lox is 1.4 mm×1.4 mm. FIG. 2 reflects the penetration depth of the formulation of the present invention, Example 11 into the pig ear. As it can be readily seen, the composition of the present invention showed a much greater penetration depth than those of the comparative Examples (illustrated by arrow).

Figure 3:
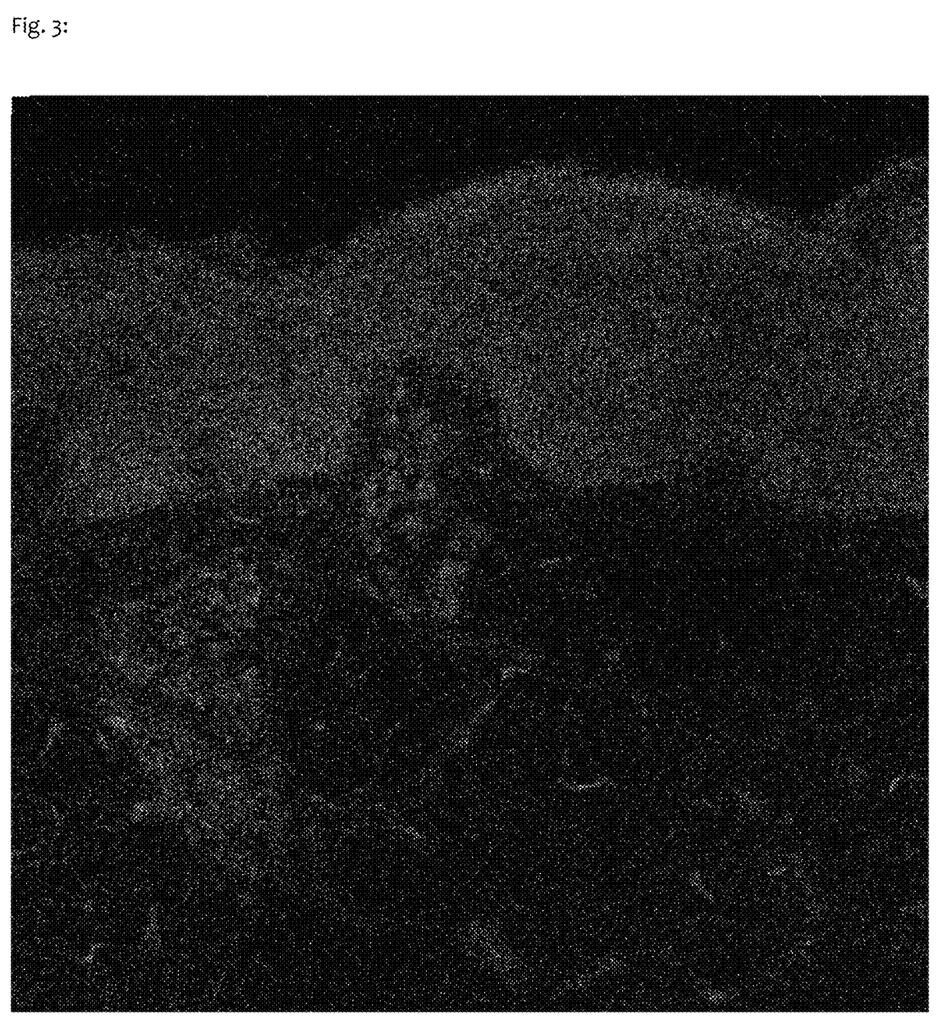
FIG. 3—depicts porphyrin fluorescence signal at 614-643 nm of Example 12 after an incubation period of 15 Min.
Figure 4:
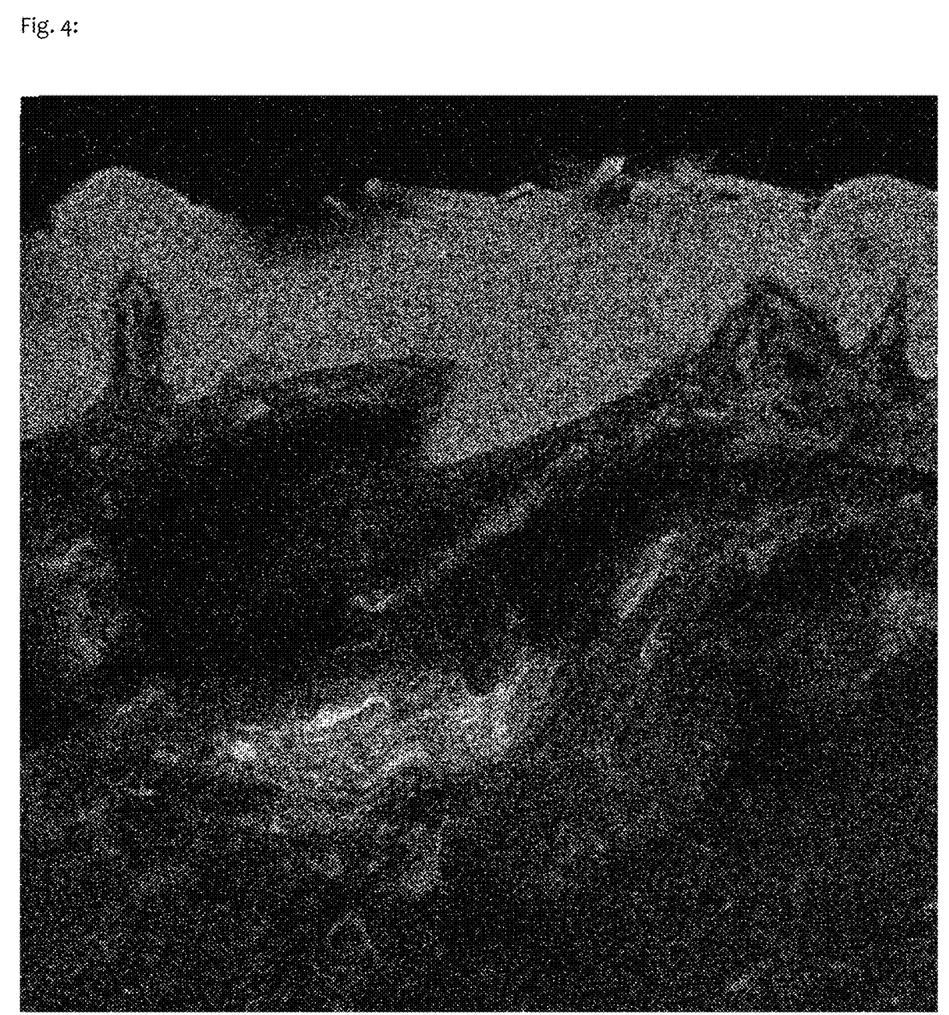
FIG. 4—depicts porphyrin fluorescence signal at 614-643 nm of Example 12 after an incubation period of 60 Min.
Figure 5:
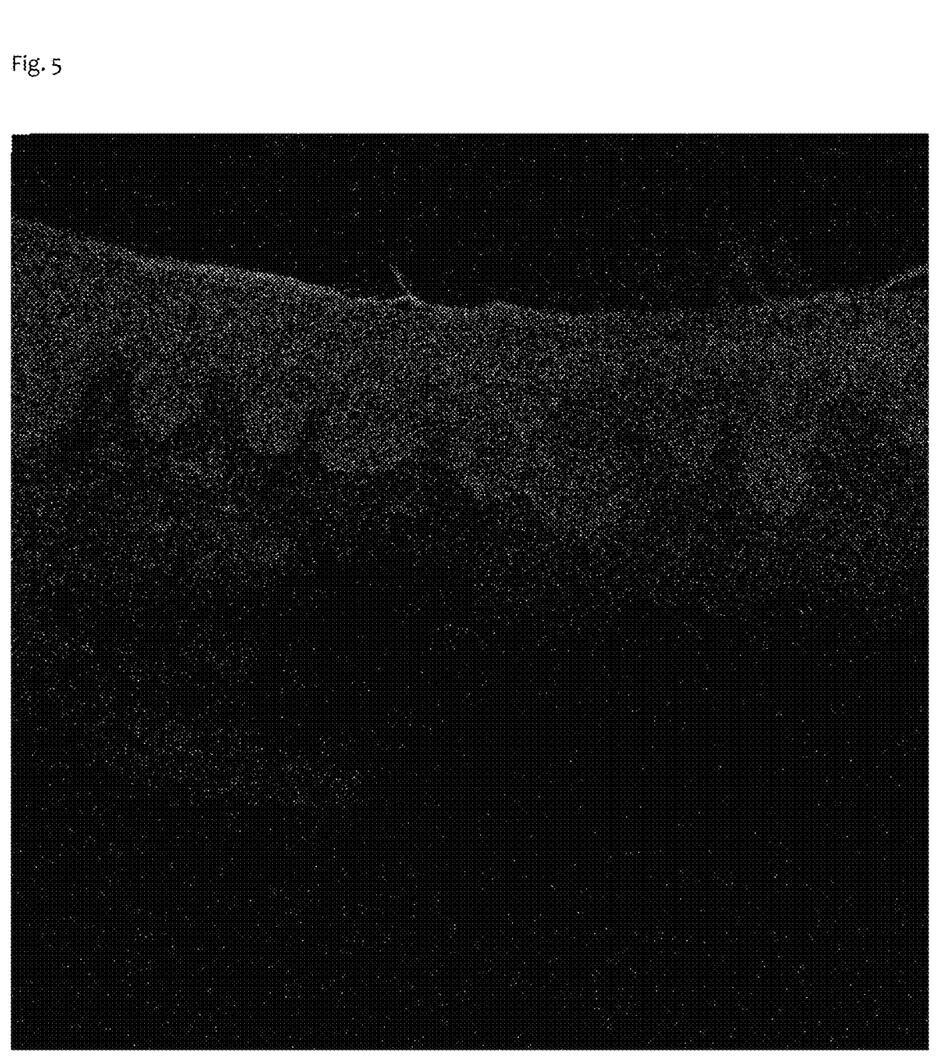
FIG. 5—depicts porphyrin fluorescence signal at 614-643 nm of Levulan® Kerastick after an incubation period of 15 Min.
Figure 6:
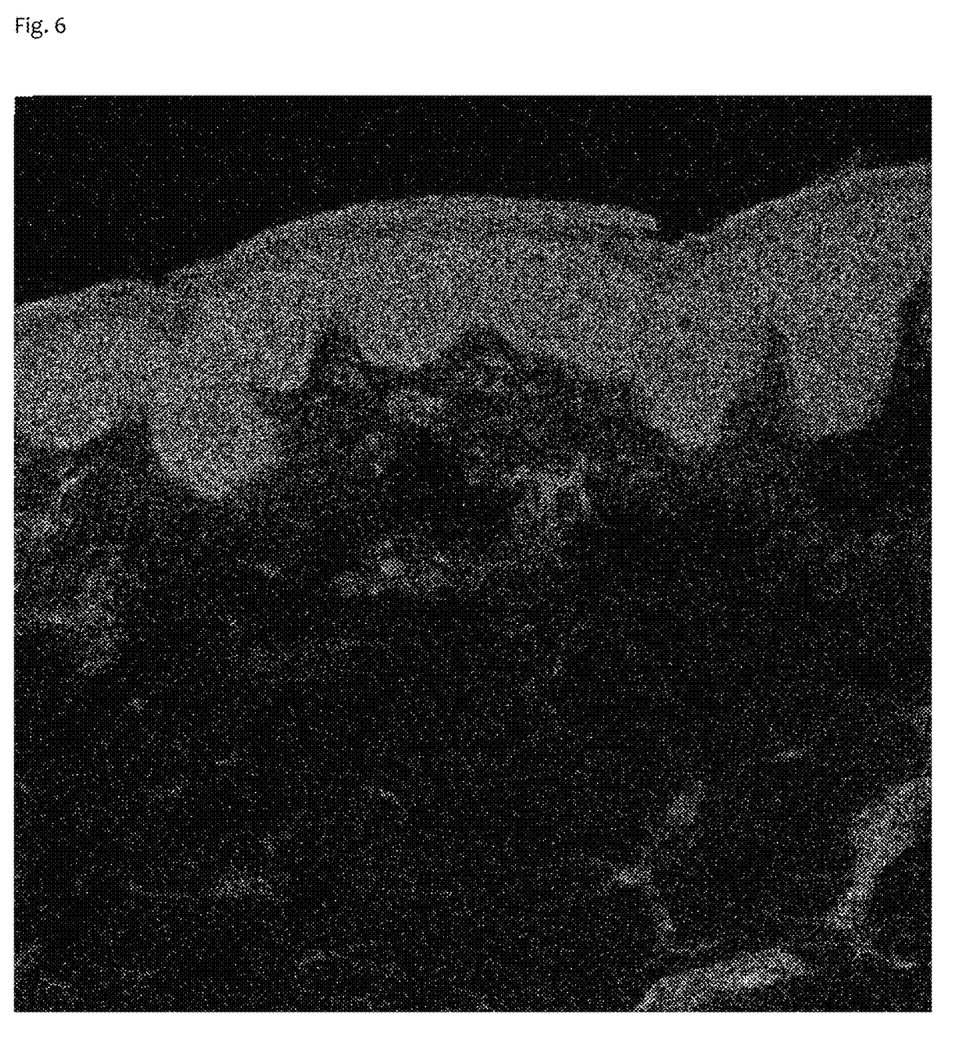
FIG. 6—depicts porphyrin fluorescence signal at 614-643 nm of Levulan® Kerastick after an incubation period of 60 Min.

Also by confocal laserscanning microscope imaging, but by using a 20× objective, the pictures for FIG. 3 up to FIG. 6 were taken. The picture size illustrates top layer pig ear as resulting by the chosen magnification objective of 20× is 0.7 mm×0.7 mm. FIG. 3 shows the Prophyrin intensity distribution for the composition of Example 12 in the epidermal layer after 15 min incubation time and FIG. 4 after 60 min incubation time. For comparison, FIG. 5 depicts the Levulan® Kerastick Porphyrin intensity distribution of the epidermal layer after 15 min incubation time and FIG. 6 after 60 min incubation time. It is evident that significant Prophyrin signals could be detected in the epidermal layer and even deeper than that which were found to be much stronger in comparison to a commercially available formulation. This demonstrates the result of the unique penetration mechanism of the described invention in terms of a faster distribution and metabolization of the 5-ALA molecule to the therapeutic useful Porphyrin photosensitizer for PDT treatment.

The invention claimed is:

1. A composition comprising
   a) 5-amino-4-oxo-pentanoic acid (5-aminolevulinic acid or 5-ALA) or the HCl salt (5-ALA-HCl) thereof as an active ingredient;
   b) 4-15% (w/w) of a first penetration enhancer selected from one or more non-ethoxylated water-miscible ether compounds selected from: 1,4:3,6-dianhydrosorbitol 2,5-pentylethylether (pentylethyl isosorbide), 1,4:3,6-dianhydrosorbitol 2,5-laurylglycerylether (laurylglyceryl isosorbide) and 1,4:3,6-dianhydrosorbitol 2,5-dimethylether (dimethyl isosorbide); and
   c) 0.5-0.15% (w/w) of a second penetration enhancer from a glycosaminoglycan compound: sodium hyaluronate.

2. The composition of claim 1, where the active ingredient is 5-aminolevulinic acid in its hydrochloride salt form (5-ALA HCl), and is contained in the composition in a concentration range of 5-30% (w/w) based on the overall weight of the composition.

3. The composition of claim 1, which is a pharmaceutical composition and comprises one or more pharmaceutically acceptable auxiliaries.

4. The composition of claim 3, which is a topical composition in form of a low viscous hydrogel, where the low viscous hydrogel has a viscosity of about 1,000-13,000 mPas at 32° C.

5. The composition of claim 1, which is low viscous hydrogel and contains 5-ALA HCl, dimethyl isosorbide and sodium hyaluronate.

6. The composition of claim 5, containing 5-ALA HCl in an amount of about 20% (w/w), dimethyl isosorbide in an amount of about 10% (w/w) and sodium hyaluronate in an amount of about 1% (w/w).

7. The composition of claim 1, which further comprises one or more preservatives, chelating agents and/or buffering agents/acidity regulators.

8. A method for photochemotherapeutic treatment or diagnosis of disorders or abnormalities of internal or external surfaces of the body, comprising administering or applying the composition of claim 1.

9. The method of claim 8, wherein the disorders or abnormalities of internal or external surfaces of the body are selected from pre-cancer and cancers, pre-cancerous lesions of the skin and other types of non-melanoma skin cancer, SCC (squamous cell carcinoma), or BCC (basal cell carcinoma).

10. The composition of claim 1, where the active ingredient is 5-aminolevulinic acid in its hydrochloride salt form (5-ALA HCl), and is contained in the composition in a concentration range of 10-25% (w/w) based on the overall weight of the composition.

11. The composition of claim 3, which is a topical composition in form of a low viscous hydrogel.

12. The composition of claim 1, wherein the one or more non-ethoxylated water-miscible ether compounds are contained in the composition in a concentration range of 8-12% (w/w) based on the overall weight of the composition.

13. The composition of claim 1, wherein the glycosaminoglycan compound: sodium hyaluronate is contained in the composition in a concentration range of 0.8-1.2% (w/w) based on the overall weight of the composition.

14. The method of claim 8, wherein the disorders or abnormalities of internal or external surfaces of the body are pre-cancerous lesions of the skin being Actinic Keratosis.

15. The composition of claim 5, wherein the dimethyl isosorbide is in an amount of about 10% (w/w) or more.

* * * * *

UNITED STATES PATENT AND TRADEMARK OFFICE
CERTIFICATE OF CORRECTION

PATENT NO. : 10,786,571 B2
APPLICATION NO. : 15/761623
DATED : September 29, 2020
INVENTOR(S) : Andre Solioz, Frank Stowasser and Armin Zimmer Page 1 of 1

It is certified that error appears in the above-identified patent and that said Letters Patent is hereby corrected as shown below:

Claim 1, Column 10, Line 65 reads:
"0.5-0.15%"
Should read:
--0.5-1.5%--.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*